United States Patent [19]

Cook et al.

[11] Patent Number: 5,202,475

[45] Date of Patent: * Apr. 13, 1993

[54] PROCESS FOR PREPARATION OF CYCLOHEXANEDICARBOXYLIC ACID

[75] Inventors: Steven L. Cook, Kingsport; Gether Irick, Jr., Gray; Crispen S. Moorehouse, Kingsport, all of Tenn.

[73] Assignee: Eastman Kodak Company, Rochester, N.Y.

[*] Notice: The portion of the term of this patent subsequent to Jun. 2, 2009 has been disclaimed.

[21] Appl. No.: 831,124

[22] Filed: Feb. 4, 1992

Related U.S. Application Data

[63] Continuation-in-part of Ser. No. 760,680, Sep. 16, 1991, Pat. No. 5,118,841, which is a continuation-in-part of Ser. No. 588,787, Sep. 27, 1990, abandoned.

[51] Int. Cl.$^5$ ............................................. C07C 61/09
[52] U.S. Cl. ...................................................... 562/509
[58] Field of Search ........................................ 562/509

[56] References Cited

U.S. PATENT DOCUMENTS

| | | |
|---|---|---|
| 2,828,335 | 3/1958 | Ferstandig . |
| 3,326,972 | 6/1967 | Schenk .............................. 562/509 |
| 3,444,237 | 5/1969 | Jaffe . |
| 3,607,917 | 9/1971 | Buls ..................................... 562/509 |
| 5,118,841 | 6/1992 | Cook ................................... 562/509 |

OTHER PUBLICATIONS

Groggins, "Unit Processes in Organic Synthesis," 5th Ed., pp. 555–560, 574–583 & 608–612 (1958).
"Kirk-Othmer Encyclopedia of Chemical Technology", 2nd Ed., vol. 6, pp. 510–511 (1965).

*Primary Examiner*—Michael L. Shippen
*Attorney, Agent, or Firm*—Charles R. Martin; William P. Heath, Jr.

[57] ABSTRACT

A process for preparation of 1,3- or 1,4-cyclohexanedicarboxylic acid comprising (A) preparing a solution comprised of the disodium salt of terephthalic acid or isophthalic acid and water, (B) continuously preparing the disodium salt of 1,3- or 1,4-cyclohexanedicarboxylic acid by continuously contacting the solution with hydrogen and the combination of ruthenium metal and a carbon support in a packed column, (C) preparing 1,3- or 1,4-cyclohexanedicarboxylic acid by contacting the disodium salt of 1,3- or 1,4-cyclohexanedicarboxylic acid with sulfuric acid or hydrochloric acid, and (D) recovering the 1,3- or 1,4-cyclohexanedicarboxylic acid by crystallization of the 1,3- or 1,4-cyclohexanedicarboxylic acid.

2 Claims, No Drawings

PROCESS FOR PREPARATION OF CYCLOHEXANEDICARBOXYLIC ACID

This application is a continuation-in-part of Ser. No. 07/760,680, filed Sep. 16, 1991 now U.S. Pat. No. 5,118,841, which was a continuation-in-part of Ser. No. 07/588,787, filed Sep. 27, 1990, now abandoned.

This invention relates to a process for preparation of 1,3- or 1,4-cyclohexanedicarboxylic acid wherein the hydrogenation step is conducted continuously.

It is well known in the art that 1,3- and 1,4-cyclohexanedicarboxylic acid can be prepared from terephthalic acid and isophthalic acid by preparing a aqueous solution of the disodium salt of terephthalic acid or iso-phthalic acid, reducing the aromatic ring using a ruthenium catalyst, preparing the acid form by contacting the disodium salt with sulfuric acid and recovering the cyclohexanedicarboxylic acid by crystallization. Typical of this art is U.S. Pat. No. 3,444,237 and U.S. Pat. No. 2,838,335.

We have now discovered a process which results in a very high yield of cyclohexanedicarboxylic acid. In the process of this invention the yield of cyclohexanedicarboxylic acid is at least 85% preferably 90% and most preferably 95%.

Broadly, the process of our invention can be described as a process for preparation of 1,3- or 1,4-cyclohexanedicarboxylic acid comprising (A) preparing a solution which has a pH in the range of 7 to 13, a temperature in the range of 20° to 100° and is comprised of 0.5 to 30.0 weight percent of the disodium salt of terephthalic acid or isophthalic acid and 99.5 to 70.0 weight percent water, (B) continuously preparing the disodium salt of 1,3- or 1,4-cyclohexanedicarboxylic acid by continuously contacting the solution with a combination of ruthenium metal and a carbon support in a packed column at a pressure in the range of 100 psig to 2,000 psig and a temperature in the range of 20° to 200° C., (C) preparing 1,3- or 1,4-cyclohexanedicarboxylic acid by contacting the disodium salt of 1,3- or 1,4-cyclohexanedicarboxylic acid with sulfuric acid or hydrochloric acid at pressure in the range of atmospheric to 40 psig, and (D) recovering the 1,3- or 1,4-cyclohexanedicarboxylic acid by crystallization of the 1,3- or 1,4-cyclohexanedicarboxylic acid in less than 60 minutes, at a temperature in the range of 130° to 20° C.

In the first step of the invention, an aqueous solution of the disodium salt of terephthalic acid or isophthalic acid is prepared. Preferably the solution is formed by combining terephthalic acid or isophthalic acid with an aqueous solution of sodium hydroxide. The sodium hydroxide and terephthalic acid or isophthalic acid reacts to form the corresponding disodium salt in accordance with well known chemistry. This step can be practiced in commercial equipment well known in the art on either a batch or continuous basis. Preferably this step is practiced continuously by the use of two stirred vessels in series because pH can most effectively be used to control the final amount of sodium hydroxide in a very precise manner.

During the first step, the pH is maintained in the range of 7 to 13, preferably 9 to 11, by adding additional water using conventional means. The temperature is maintained in the range of 20° to 100°, preferably 40° to 90° C.

The amount of disodium salt in the solution can vary from 0.5 to 30.0, preferably 10 to 18, weight percent, based on the weight of the water and disodium salt being 100%. The amount of disodium salt depends on whether the disodium salt of isophthalic acid or terephthalic acid is desired. If isophthalic acid is used, the amount of disodium salt is preferably around 16% due to processing conditions required for the reduced product. If terephthalic acid is used, the amount of disodium salt is preferably around 12% due to solubility limitations.

After the solution of water and disodium salt of terephthalic acid or isophthalic acid is prepared in the first step, the disodium salt of 1,3- or 1,4-cyclohexanedicarboxylic acid is prepared in the second step by reducing the aromatic ring by continuously contacting the solution with hydrogen and a combination of ruthenium metal and a carbon support in a packed column.

The type of packed column is not particularly important as long as the column functions as a fixed bed such that the liquid reactant passes over the catalyst to provide good gas/liquid/solid mass transfer conditions.

Preferably hydrogen and the solution from the first step are introduced into the top of the packed column and the solution descends under the influence of gravity through the column in accordance with so-called "trickle bed" technology.

Packed columns of the type well known in the art are suitable for conducting this step. Preferably two columns are used in series because the crush strength of most carbon catalyst supports limits the bed height.

The pressure in the packed column is in the range of 100 to 2,000 psig, preferably 1,500 to 2,000 psig.

The temperature in the packed column is in the range of 20° to 200° C.

The combination of ruthenium metal and a carbon support is well known in the art and is described in Sci. Repts. Moscow State University., No. 6, 347-52.

The use of the combination of ruthenium and a carbon support in continuous operation is an important feature of this invention. The use of the combination of ruthenium metal and a carbon support is thought to be patentable over the prior art due to the difference between the batch and continuous performance of the combination of ruthenium metal and a carbon support and ruthenium metal and an alumina support. More specifically, when the reduction step is conducted on a batch basis the combination of ruthenium metal on an alumina support results in superior yields compared to the combination of ruthenium metal and a carbon support. Thus, since the combination of ruthenium metal and an alumina support is a superior catalyst over the combination of ruthenium metal and a carbon support in batch operation it would be thought that the performance of the combination of ruthenium metal and an alumina support would also be superior to the combination of ruthenium metal and a carbon support in continuous operation and would therefore exhibit enhanced catalyst life. Surprisingly, just the opposite occurs. In continuous operation, the life of the catalyst comprised of the claimed combination of ruthenium metal and a carbon support is significantly longer than the life of the catalyst comprised of the combination of ruthenium metal and an alumina support.

Laboratory work has established that in batch operation the performance of the combination of ruthenium metal and an alumina support is a superior catalyst compared to the performance of the combination of ruthenium metal and a carbon support.

In this laboratory work the behavior of the combination of ruthenium metal and an alumina support in the reduction of the disodium salt of terephthalic acid to the disodium salt of 1,4-cyclohexanedicarboxylic acid in a batch process was investigated by the following procedure. A rocking autoclave was charged with 200 mL of water, 10.0 g of terephthalic acid, 4.88 g of NaOH, and 1.5 g of 5% ruthenium metal on an alumina support. The reactor was pressurized to 500 psig with hydrogen and the temperature raised to 165 degrees centigrade. The hydrogen pressure was increased to 1,200 psig and the rocking mechanism turned on. After 2.0 hours the heat and rocking motor were turned off and the reactor cooled with air. After venting off the hydrogen pressure the contents were removed and the catalyst filtered out through two layers of filter paper. The clear filtrate was acidified to pH 1 with aqueous HCl, cooled to 5 degrees centigrade in an ice bath, the crystallized solid filtered, washed with water, and suction dried to give 5.05 g of 1,4-cyclohexane-dicarboxylic acid. The filtrate was concentrated on a rotary evaporator until solids were apparent. The 1,4-Cyclohexane-dicarboxylic acid isolated as described above weighed 3.3 g after drying for a yield of 81% of the theoretical amount.

The behavior of the combination of ruthenium metal and a carbon support in the reduction of the disodium salt of terephthalic acid to the disodium salt of 1,4-cyclohexanedicarboxylic acid in a batch process was investigated by the following procedure. A rocking autoclave was charged with 200 mL of water, 10.0 g of terephthalic acid, 4.88 g of NaOH, and 1.5 g of 5% ruthenium metal on a carbon support. The reactor was pressurized to 500 psig with hydrogen and the temperature raised to 165 degrees centigrade. The hydrogen pressure was increased to 1,200 psig and the rocking mechanism turned on. After 2.0 hours the heat and rocking motor were turned off and the reactor cooled with air. After venting off the hydrogen pressure the contents were removed and the catalyst filtered out through two layers of filter paper. The clear filtrate was acidified to pH 1 with aqueous HCl, cooled to 5 degrees centigrade in an ice bath, the crystallized solid filtered, washed with water, and suction dried to give 5.45 g of 1,4-cyclohexane-dicarboxylic acid. The filtrate was concentrated on a rotary evaporator until solids were apparent. The 1,4-cyclohexanedicarboxylic acid isolated as described above weighed 2.6 g after drying for a yield of 78% of the theoretical amount.

Surprisingly, laboratory work has established that in continuous operation the life of the combination of ruthenium metal and a carbon support is superior to the life of the combination of ruthenium metal and an alumina support.

In this work the combination of ruthenium metal and an alumina support was used in the reduction of the disodium salt of terephthalic acid to the disodium salt of 1,4-cyclohexanedicarboxylic acid in a continuous process in accordance with step (B) of claim 1 of the application. A column 2' long having a 1" inside diameter was packed with 1% ruthenium metal on a granular alumina support to form a trickle bed reactor. A solution of 150 g terephthalic acid, 80 g NaOH and 2,775 g of water was continuously introduced into the reactor at a temperature of 150° C. and a rate of 400 mL/h. The reactor was operated at a pressure of 1,250 psig and the off gas purge rate was 1.2 cubic feet/hour. Samples were periodically taken over a thirty hour period, acidified to pH 1 and cooled. The initial conversion to 1,4-cyclohexane-dicarboxylic acid was 89.8% of theoretical amount. After about 30 hours the conversion dropped to approximately 75%.

In this work the behavior over time of the combination of ruthenium metal and a carbon support in the reduction of the disodium salt of terephthalic acid to the disodium salt of 1,4-cyclohexanedicarboxylic acid was investigated in a continuous process in accordance with step (B) of claim 1 of the application. The same trickle-bed reactor described above was charged with 126 g of 1% ruthenium on a carbon support. The same solution described above was continuously introduced into the reactor at a temperature of 160° C. and a rate of 590 mL/h. The reactor was operated at a pressure of 1,250 psig and the off gas purge rate was 1.2 cubic feet/hour. Samples were periodically taken over a thirty hour period, acidified to pH 1 and cooled. The initial conversion to 1,4-cyclohexanedicarboxylic acid was 98.8% of theoretical amount. After about 30 hours the conversion was approximately 96%. After 76 hours the conversion was approximately 75%.

In summary, this laboratory work establishes that the yield from batch operation using the combination of ruthenium metal and an alumina support was 81% and the yield using the combination of ruthenium metal and a carbon support was 78%. In distinction, when continuous operation is used the life of the catalyst comprised of the combination of ruthenium metal and a carbon support was represented by a reduction in yield to only 96% after 30 hours and it required 76 hours for the yield to fall to the 75% value while the life of the catalyst comprised of the combination of ruthenium metal and an alumina support was represented by an initial yield of only 89.9% and a reduction in yield to only 75% after 30 hours.

In the third step, 1,3- or 1,4-cyclohexanedicarboxylic acid is prepared by contacting the disodium salt of 1,3- or 1,4-cyclohexanedicarboxylic acid with sulfuric acid or hydrochloric acid.

This step can be conducted in standard stirred vessels well known in the art. Typically, the aqueous solution containing 1,4- or 1,3-cyclohexanedicarboxylic acid resulting from the second step is continuously introduced into a stirred vessel along with sulfuric acid. The pressure is maintained in the range of atmosphere to 40 psig. The temperature is maintained at least 80° C.

Preferably this step is practiced continuously wherein two vessels are used in series because pH can be used to control the final amount of sulfuric acid in a very precise manner. A final pH of 2.8 is most preferred in the case of 1,4-cyclohexanedicarboxylic acid, while a pH of 2.6 is most preferred in the case of 1,3-cyclohexanedicarboxylic acid.

In the fourth step 1,3- or 1,4-cyclohexanedicarboxylic acid is recovered by crystallization of the 1,3- or 1,4-cyclohexanedicarboxylic acid. This step is preferably performed continuously in conventional equipment such as a continuously circulated crystallizer.

The temperature is in the range of about 110° to 20° C., preferably about 110° to 65° C. The pressure is in the range of 15 to 0.1 psig.

We claim:

1. A process for preparation of 1,3- or 1,4-cyclohexanedicarboxylic acid comprising (A) preparing a solution which has a pH in the range of 7 to 13, a temperature in the range of 20° to 100° and is comprised of 0.5 to 30.0 weight percent of the disodium salt of terephthalic acid or isophthalic acid and 99.5 to 70.0 weight percent water, (B) continuously preparing the disodium salt of 1,3- or 1,4-cyclohexanedicarboxylic acid by continuously contacting the solution with hydrogen and the combination of ruthenium metal and a carbon support in a packed column at a pressure in the range of 100 psig to 2,000 psig and a temperature in the range of 20° to 200° C., (C) preparing 1,3- or 1,4-cyclohexanedicarboxylic acid by contacting the disodium salt of 1,3- or 1,4-cyclohexanedicarboxylic acid with a sulfuric acid or hydrochloric acid at a pressure in the range of atmospheric to 40 psig, and (D) recovering the 1,3- or 1,4-cyclohexanedicarboxylic acid by crystallization of the 1,3- or 1,4-cyclohexanedicarboxylic acid at a temperature in the range of about 110° to 20° C. and a pressure in the range of 15 to 0.1 psig.

2. A process for preparation of 1,3- or 1,4-cyclohexanedicarboxylic acid comprising (A) preparing a solution which has a pH in the range of 9 to 11, a temperature in the range of 40° to 90° and is comprised of 10 to 18 weight percent of the disodium salt of terephthalic acid or isophthalic acid and 90 to 82 weight percent water, (B) continuously preparing the disodium salt of 1,3- or 1,4-cyclohexanedicarboxylic acid by continuously contacting the solution with hydrogen and the combination of ruthenium metal and a carbon support in a packed column at a pressure in the range of 1,500 psig to 2,000 psig and a temperature in the range of 20° to 200° C., (C) preparing 1,3- or 1,4-cyclohexanedicarboxylic acid by contacting the disodium salt of 1,3- or 1,4-cyclohexanedicarboxylic acid with sulfuric acid or hydrochloric acid at a pressure in the range of atmospheric to 40 psig, and (D) recovering the 1,3- or 1,4-cyclohexanedicarboxylic acid by crystallization of the 1,3- or 1,4-cyclohexanedicarboxyic acid at a temperature in the range of 120° to 65° C.

* * * * *